United States Patent
Parris et al.

(10) Patent No.: US 11,517,519 B2
(45) Date of Patent: Dec. 6, 2022

(54) PROCESS FOR TREATING KERATIN FIBRES WITH A PARTICULAR COMPOSITION AND A HEATING TOOL

(71) Applicant: L'Oreal, Paris (FR)

(72) Inventors: Eric Parris, Saint-Ouen (FR); Gabin Vic, Saint-Ouen (FR); Frédéric Woodland, Saint-Ouen (FR)

(73) Assignee: L'OREAL, Paris (FR)

( * ) Notice: Subject to any disclaimer, the term of this patent is extended or adjusted under 35 U.S.C. 154(b) by 38 days.

(21) Appl. No.: 16/307,185

(22) PCT Filed: Jun. 6, 2017

(86) PCT No.: PCT/EP2017/063659
§ 371 (c)(1),
(2) Date: Dec. 5, 2018

(87) PCT Pub. No.: WO2017/211786
PCT Pub. Date: Dec. 14, 2017

(65) Prior Publication Data
US 2019/0142731 A1  May 16, 2019

(30) Foreign Application Priority Data

Jun. 6, 2016  (FR) ...................................... 1655165

(51) Int. Cl.
| A61K 8/92 | (2006.01) |
| A61K 8/41 | (2006.01) |
| A61K 8/898 | (2006.01) |
| A61Q 5/06 | (2006.01) |
| A45D 7/06 | (2006.01) |

(52) U.S. Cl.
CPC .............. *A61K 8/922* (2013.01); *A61K 8/416* (2013.01); *A61K 8/898* (2013.01); *A61Q 5/06* (2013.01); *A45D 7/06* (2013.01); *A61K 2800/30* (2013.01); *A61K 2800/524* (2013.01); *A61K 2800/5426* (2013.01)

(58) Field of Classification Search
CPC .................. A45D 7/06; A61K 2800/30; A61K 2800/524; A61K 2800/5426; A61K 8/416; A61K 8/898; A61K 8/922; A61Q 5/06
See application file for complete search history.

(56) References Cited

U.S. PATENT DOCUMENTS

| 4,031,307 A | 6/1977 | DeMartino et al. |
| 4,131,576 A | 12/1978 | Iovine et al. |
| 4,137,180 A | 1/1979 | Naik et al. |
| 4,165,367 A | 8/1979 | Chakrabarti |
| 4,874,554 A | 10/1989 | Lange et al. |
| 4,957,732 A | 9/1990 | Grollier et al. |
| 7,115,254 B1 * | 10/2006 | Brandt ................. A61K 8/8182 424/70.2 |
| 9,408,785 B2 * | 8/2016 | Pistorio ..................... A61Q 5/06 |
| 2006/0201924 A1 * | 9/2006 | Hirata et al. ............. A45D 1/04 219/225 |
| 2007/0134186 A1 * | 6/2007 | Mezure et al. .......... A61K 8/72 424/70.11 |
| 2009/0092567 A1 * | 4/2009 | Chou ....................... A61Q 1/06 424/64 |
| 2014/0102468 A1 * | 4/2014 | Pistorio .................. A61K 8/025 424/401 |
| 2015/0290109 A1 * | 10/2015 | Simonnet ............. A61K 8/0241 132/202 |
| 2016/0309868 A1 | 10/2016 | Parris et al. |

FOREIGN PATENT DOCUMENTS

| DE | 10 2013 225454 A1 | 4/2014 |
| EP | 0186507 A2 | 7/1986 |
| EP | 0342834 A2 | 11/1989 |
| FR | 1492597 A | 8/1967 |
| FR | 2077143 A5 | 10/1971 |
| FR | 2393573 A1 | 1/1979 |
| FR | 2983725 A1 | 6/2013 |
| FR | 3015195 A1 | 6/2015 |
| WO | 2008/156459 A1 | 12/2008 |
| WO | 2012/175734 A1 | 12/2012 |
| WO | 2014/060405 A2 | 4/2014 |
| WO | 2015/091043 A2 | 6/2015 |

OTHER PUBLICATIONS

DE 10 2010 225454 A1 machine translation; Apr. 17, 2014.*
International Search Report for counterpart Application No. PCT/EP2017/063659, dated Aug. 21, 2017.
Marcant, Melanie, "Merquat™ Polymers for Heat Protection of Keratin," IP.Com Journal, IP.Com Inc., West Henrietta, NY, Mar. 30, 2016.
Unknown: "Thermal Hair Straightening: Supporting Claims About the Benefits of Silicones," XP055322932, Oct. 1, 2015. Retrieved from Internet: http://www.momentive.com/discover/news-and-press-releases/Thermal-Hair-Straightening.pdf [retrieved Nov. 24, 2016].

* cited by examiner

*Primary Examiner* — Jeffrey T. Palenik
(74) *Attorney, Agent, or Firm* — The Marbury Law Group, PLLC.

(57) ABSTRACT

The present invention relates to a process for treating human keratin fibres such as the hair, which comprises: i) a step of applying to the human keratin fibres a composition comprising: —at least one plant wax: —at least 60% by weight of water relative to the total weight of the composition; ii) followed by a step of heating the keratin fibres by means of a heating appliance at a temperature ranging from 80° C. to 160° C., preferably from 110° C. to 50° C., more preferably from 120° C. to 150° C., which is moved along the fibres, iii) optionally followed by a step of rinsing the keratin fibres.

18 Claims, No Drawings

PROCESS FOR TREATING KERATIN FIBRES WITH A PARTICULAR COMPOSITION AND A HEATING TOOL

CROSS REFERENCE TO RELATED APPLICATIONS

This is a national stage application of PCT/EP2017/063659, filed internationally on Jun. 6, 2017, which claims priority to French Application No. 1655165, filed on Jun. 6, 2016, both of which are incorporated by reference herein in their entireties.

The invention relates to a process for treating keratin fibres, especially the hair, with input of heat.

Hair may be damaged or embrittled by the action of external atmospheric agents such as light and bad weather, or by mechanical or chemical treatments, such as brushing, combing, dyeing, bleaching, permanent-waving and/or relaxing.

To overcome these drawbacks, it is common practice to make use of hair treatments which can condition the hair. These haircare compositions may be conditioning shampoos or hair conditioners, which may be in the form of hair gels or lotions or more or less thick creams. They generally contain conditioning agents, intended mainly to repair or to limit the harmful or undesirable effects brought about by the various treatments or attacks to which hair fibres are more or less repeatedly subjected.

To further improve the level of conditioning provided to the hair, it has already been proposed to combine the use of a care composition comprising a conditioning agent with a heating step.

EP 2 723 307 has, for example, already proposed a hair treatment process combining the application of a care composition comprising conditioning agents with a step of heating the composition on the hair in a confined space. The hair onto which the composition is applied is thus inserted into an occlusive space and subjected to heat for a treatment time, without moving the heating tool. This process makes it possible especially to improve the penetration of the conditioning agents on the hair.

There is a need for a process which further improves the level of conditioning of the hair while at the same time being easy to apply.

There is especially an expectation of a better cosmetic result, greater speed of treatment and/or improvement of the persistence of the effects over time, especially persistence of the effects with respect to washing.

The aim of the present invention is to propose such a hair treatment process, making it possible to obtain both immediate and persistent conditioning.

Thus, one subject of the invention is a process for treating keratin fibres, especially the hair, which comprises:
i) a step of applying to the keratin fibres a composition comprising:
at least one plant wax:
at least 60% by weight of water relative to the total weight of the composition;
ii) followed by a step of heating the keratin fibres by means of a heating appliance at a temperature ranging from 80° C. to 160° C., preferably from 110° C. to 150° C., more preferably from 120° C. to 150° C., which is moved along the fibres, iii) optionally followed by a step of rinsing the keratin fibres.

The implementation of the process according to the invention makes it possible especially to obtain the desired properties, immediately on application, and in particular a homogeneous feel, reduction of split ends, improved suppleness and improved ease of disentangling.

The properties afforded by the process according to the invention are also particularly long-lasting. They are particularly long-lasting when washed with shampoo, in particular for at least 4 washes.

In the present description, the expression "at least one" is equivalent to the expression "one or more" and can substitute for said expression, and the expression "between" is equivalent to the expression "ranging from" and can substitute for said expression, and implies that the limits are included.

The process according to the invention comprises a step of applying to keratin fibers such as the hair a composition comprising at least 60% of water and at least one plant wax.

The composition used in the process according to the invention comprises one or more plant waxes.

According to the present patent application, the term "wax" means a lipophilic compound that is solid at room temperature (25° C.) and at atmospheric pressure (1.013× $10^5$ Pa), with a reversible solid/liquid change of state, having a melting point of greater than or equal to 30° C., which may be up to 200° C. and especially up to 120° C.

By bringing a wax to the liquid state (melting), it is possible to make it miscible with the other ingredients of the composition and to form a macroscopically homogeneous mixture, but on returning the temperature of the mixture to room temperature, recrystallization of the wax in the mixture is obtained.

For the purposes of the invention, the melting point corresponds to the temperature of the most endothermic peak observed on thermal analysis (differential scanning calorimetry or DSC) as described in standard ISO 11357-3; 1999. The melting point of the wax may be measured using a differential scanning calorimeter (DSC), for example the calorimeter sold under the name MDSC 2920 by the company TA Instruments.

The measurement protocol is as follows:

A sample of 5 mg of wax placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The plant wax used in the compositions may be chosen from carnauba wax, candelilla wax such as the product sold under the reference SP 75 G by the company Strahl & Pitsch, alfalfa wax, jojoba wax, *mimosa* wax, rice wax, soybean wax, orange blossom wax, jasmine wax, rose wax, olive wax, rice wax such as the product sold under the reference NC 1720 by the company Cera Rica Noda, ouricury wax, Berry wax, Japan wax, sumac wax, orange wax, lemon wax, cocoa butter, palm butter, cork fibre wax or sugarcane wax, the sunflower seed wax sold by the company Koster Keunen under the reference Sunflower Wax, absolute waxes of flowers such as the essential wax of blackcurrant blossom sold by the company Bertin (France).

Mention may also be made of waxes obtained by catalytic hydrogenation of plant oils containing linear or branched C8-C32 fatty chains. Among these, mention may be made especially of isomerized jojoba oil such as the trans-isomerized partially hydrogenated jojoba oil, especially the product manufactured or sold by the company Desert Whale under the trade reference Iso-Jojoba-50®, hydrogenated sunflower oil, hydrogenated castor oil and hydrogenated coconut oil.

The waxes obtained by hydrogenation of castor oil esterified with cetyl alcohol, such as those sold under the names Phytowax Castor 16L64® and 22L73® by the company Sophim, may also be used.

It is also possible to use microwaxes in the compositions of the invention; mention may be made especially of carnauba microwaxes, such as the product sold under the name MicroCare 350® by the company Micro Powders, microwaxes consisting of a mixture of carnauba wax and of polyethylene wax, such as those sold under the names MicroCare 300® and 310® by the company Micro Powders, microwaxes consisting of a mixture of carnauba wax and of synthetic wax, such as the product sold under the name MicroCare 325® by the company Micro Powders.

Preferably, the composition used in the process according to the invention comprises at least one wax chosen from carnauba wax, candelilla wax, jojoba wax and palm butter.

According to a particularly preferred embodiment, the composition comprises a candelilla wax.

The plant waxes may be present in the composition used in the process according to the invention in a content ranging from 0.25% to 25% by weight, preferably in a content ranging from 0.5% to 20% by weight and better still from 0.5% to 15% by weight relative to the total weight of the composition.

Conditioning Agents

The composition used in the process according to the invention may also comprise one or more conditioning agents other than the plant waxes, chosen from cationic surfactants, cationic polymers, silicones and non-silicone fatty substances, and mixtures thereof.

When they are present, the conditioning agents may be present in the composition in a content ranging from 0.01% to 20% by weight relative to the total weight of the composition, preferably from 0.05% to 15% by weight and more preferably from 0.1% to 10% by weight relative to the total weight of the composition.

Preferably, the composition may comprise one or more cationic surfactants.

The cationic surfactants that may be used in the composition used in the process according to the invention comprise, for example, optionally polyoxyalkylenated primary, secondary or tertiary fatty amine salts, quaternary ammonium salts, and mixtures thereof.

Examples of quaternary ammonium salts that may especially be mentioned include:

those corresponding to the general formula (A1) below:

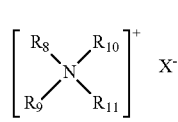

(A1)

in which formula (A1):
R8 to R11, which may be identical or different, represent a linear or branched aliphatic group comprising from 1 to 30 carbon atoms, or an aromatic group such as aryl or alkylaryl, it being understood that at least one of the groups R8 to R11 comprises from 8 to 30 carbon atoms and preferably from 12 to 24 carbon atoms; and X— represents an organic or inorganic anionic counterion, such as that chosen from halides, acetates, phosphates, nitrates, (C1-C4)alkyl sulfates, (C1-C4)alkyl- or (C1-C4)alkylarylsulfonates, in particular methyl sulfate and ethyl sulfate.

The aliphatic groups of R8 to R11 may also comprise heteroatoms especially such as oxygen, nitrogen, sulfur and halogens.

The aliphatic groups of R8 to R11 are chosen, for example, from C1-C30 alkyl, C1-C30 alkoxy, polyoxy(C2-C6)alkylene, C1-C30 alkylamide, (C12-C22)alkylamido(C2-C6)alkyl, (C12-C22)alkylacetate, and C1-C30 hydroxyalkyl groups, X— is an anionic counterion chosen from halides, phosphates, acetates, lactates, (C1-C4)alkyl sulfates, and (C1-C4)alkyl- or (C1-C4)alkylarylsulfonates.

Among the quaternary ammonium salts of formula (A1), preference is given firstly to tetraalkylammonium chlorides, for instance dialkyldimethylammonium or alkyltrimethylammonium chlorides in which the alkyl group contains from about 12 to carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyl-dimethyl(myristyl acetate)ammonium chloride, sold under the name Ceraphyl® 70 by the company Van Dyk;

quaternary ammonium salts of imidazoline, for instance those of formula (A2) below:

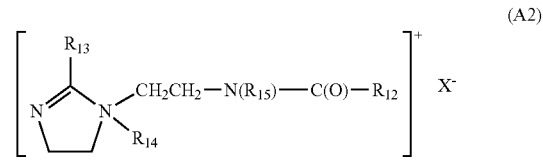

(A2)

in which formula (A2):
R12 represents an alkenyl or alkyl group comprising from 8 to 30 carbon atoms, for example tallow fatty acid derivatives;

R13 represents a hydrogen atom, a C1-C4 alkyl group or an alkenyl or alkyl group comprising from 8 to 30 carbon atoms;

R14 represents a C1-C4 alkyl group;

R15 represents a hydrogen atom or a C1-C4 alkyl group;

X— represents an organic or inorganic anionic counterion, such as that chosen from halides, phosphates, acetates, lactates, (C1-C4)alkyl sulfates, (C1-C4)alkyl- or (C1-C4)alkylarylsulfonates.

R12 and R13 preferably denote a mixture of alkenyl or alkyl groups containing from 12 to 21 carbon atoms, for example tallow fatty acid derivatives, R14 denotes a methyl group, and R15 denotes a hydrogen atom. Such a product is sold, for example, under the name Rewoquat® W 75 by Rewo;

quaternary diammonium or triammonium salts, particularly of formula (A3) below:

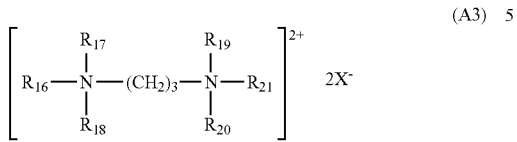

in which formula (A3):
R16 denotes an alkyl group comprising from about 16 to 30 carbon atoms, which is optionally hydroxylated and/or interrupted with one or more oxygen atoms;
R17 is chosen from hydrogen, an alkyl group comprising from 1 to 4 carbon atoms or a group —(CH2)3-N+ (R16a)(R17a)(R18a), X—;
R16a, R17a, R18a, R18, R19, R20 and R21, which may be identical or different, are chosen from hydrogen and an alkyl group comprising from 1 to 4 carbon atoms; and
X—, which may be identical or different, represent an organic or inorganic anionic counterion, such as that chosen from halides, acetates, phosphates, nitrates, (C1-C4)alkyl sulfates, (C1-C4)alkyl- or (C1-C4)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (A4) below:

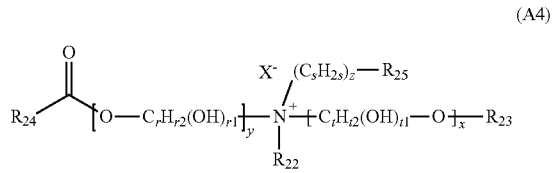

in which formula (A4):
R22 is chosen from C1-C6 alkyl groups and C1-C6 hydroxyalkyl or dihydroxyalkyl groups,
R23 is chosen from:
the group

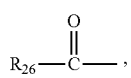

linear or branched, saturated or unsaturated C1-C22 hydrocarbon-based groups R27,
a hydrogen atom,
R25 is chosen from:
the group

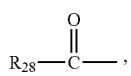

the groups R29, which are linear or branched, saturated or unsaturated C1-C6 hydrocarbon-based groups;
a hydrogen atom,
R24, R26 and R28, which are identical or different, are selected from linear or branched, saturated or unsaturated C7-C21 hydrocarbon-based groups;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers having values from 0 to 10,
X— represents an organic or mineral anionic counterion,
with the proviso that the sum x+y+z is from 1 to 15, that when x is 0 then R23 denotes R27, and that when z is 0 then R25 denotes a linear or branched, saturated or unsaturated C1-C6 hydrocarbon-based radical R29.

The alkyl groups R22 may be linear or branched, and more particularly linear.

Preferably, R22 denotes a methyl, ethyl, hydroxyethyl or dihydroxypropyl group, and more particularly a methyl or ethyl group.

Advantageously, the sum x+y+z is from 1 to 10.

When R23 is a hydrocarbon-based group R27, it may be long and contain from 12 to 22 carbon atoms, or may be short and contain from 1 to 3 carbon atoms.

When R25 is a hydrocarbon-based group R29, it preferably contains 1 to 3 carbon atoms.

Advantageously, R24, R26 and R28, which may be identical or different, are chosen from linear or branched, saturated or unsaturated C11-C21 hydrocarbon-based groups, and more particularly from linear or branched, saturated or unsaturated 011-C21 alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anionic counterion X— is preferably a halide, such as chloride, bromide or iodide; a (C1-C4)alkyl sulfate or a (C1-C4)alkyl- or (C1-C4)alkylarylsulfonate.

However, use may be made of methanesulfonate, phosphate, nitrate, tosylate, an anion derived from an organic acid, such as acetate or lactate, or any other anion that is compatible with the ammonium bearing an ester function.

The anionic counterion X— is even more particularly chloride, methyl sulfate or ethyl sulfate.

Use is made more particularly in the composition according to the invention of the ammonium salts of formula (A4) in which:
R22 denotes a methyl or ethyl group,
x and y are equal to 1,
z is equal to 0 or 1,
r, s and t are equal to 2,
R23 is chosen from:
the group

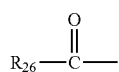

methyl, ethyl or C14-C22 hydrocarbon-based groups,
a hydrogen atom,
R25 is chosen from:
the group

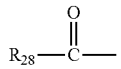

a hydrogen atom,

R24, R26 and R28, which may be identical or different, are chosen from linear or branched, saturated or unsaturated C13-C17 hydrocarbon-based groups, and preferably from linear or branched, saturated or unsaturated C13-C17 alkyl and alkenyl groups.

Advantageously, the hydrocarbon-based radicals are linear.

Among the compounds of formula (A4), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester functional group that are described in patents U.S. Pat. Nos. 4,874,554 and 4,137,180.

Use may be made of behenoylhydroxypropyltrimethylammonium chloride, provided by Kao under the name Quatarmin BTC 131.

Preferably, the ammonium salts containing at least one ester functional group contain two ester functional groups.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride and cetyltrimethylammonium chloride, and mixtures thereof.

When they are present, the cationic surfactants are present in an amount ranging from 0.01% to 15% by weight, preferably from 0.05% to 10% by weight and better still from 0.1% to 5% by weight, relative to the total weight of the composition.

The composition may also comprise one or more cationic polymers.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) homopolymers or copolymers derived from acrylic or methacrylic esters or amides and comprising at least one of the units of the following formulae:

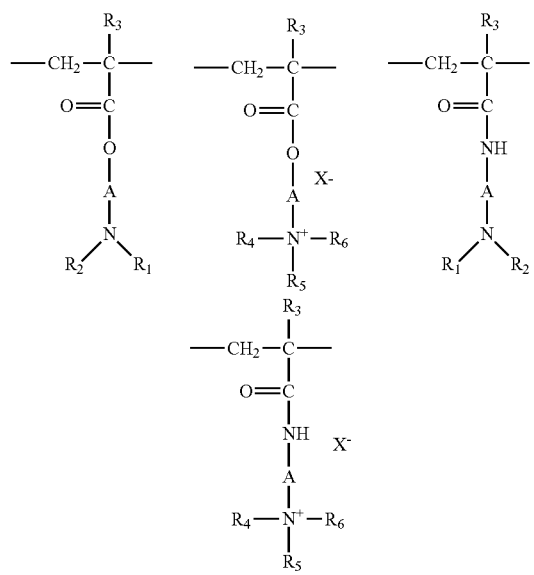

in which:

R3, which may be identical or different, denote a hydrogen atom or a CH3 radical;

A, which may be identical or different, represent a linear or branched divalent alkyl group of 1 to 6 carbon atoms, preferably 2 or 3 carbon atoms, or a hydroxyalkyl group of 1 to 4 carbon atoms;

R4, R5 and R6, which may be identical or different, represent an alkyl group containing from 1 to 18 carbon atoms or a benzyl radical, preferably an alkyl group containing from 1 to 6 carbon atoms;

R1 and R2, which may be identical or different, represent a hydrogen atom or an alkyl group containing from 1 to 6 carbon atoms, preferably methyl or ethyl;

X denotes an anion derived from a mineral or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower (C1-C4) alkyls, acrylic or methacrylic acids or esters thereof, vinyllactams such as vinylpyrrolidone or vinylcaprolactam, and vinyl esters.

Among these copolymers of family (1), mention may be made of:

copolymers of acrylamide and of dimethylaminoethyl methacrylate quaternized with dimethyl sulfate or with a dimethyl halide, such as that sold under the name Hercofloc by the company Hercules, copolymers of acrylamide and of methacryloyloxyethyltrimethylammonium chloride, such as the products sold under the name Bina Quat P 100 by the company Ciba Geigy, the copolymer of acrylamide and of methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573;

dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers, such as the copolymers sold under the name Styleze CC 10 by ISP, quaternized vinylpyrrolidone/dimethylaminopropylmethacrylamide copolymers such as the product sold under the name Gafquat HS 100 by the company ISP, preferably crosslinked polymers of methacryloyloxy(C1-C4)alkyltri(C1-C4)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba.

(2) cationic polysaccharides, especially cationic celluloses and galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in patent U.S. Pat. No. 4,131,576, and mention may be made of hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in patents U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, chloride). Such products are in particular sold under the names Jaguar C13 S, Jaguar C 15, Jaguar C 17 and Jaguar C162 by the company Rhodia.

(3) polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers.

(4) water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyaminoamide preferably of between 0.5:1 and 1.8:1. Polymers of this type are sold in particular under the name Hercosett 57 by Hercules Inc. or else under the name PD 170 or Delsette 101 by Hercules in the case of the adipic acid/epoxypropyl/diethylenetriamine copolymer.

(7) cyclopolymers of alkyldiallylamine or of dialkyldiallylammonium, such as the homopolymers or copolymers containing, as main constituent of the chain, units corresponding to formula (I) or (II):

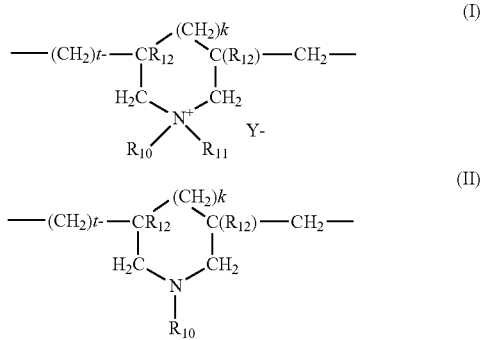

in which k and t are equal to 0 or 1, the sum k+t being equal to 1;

R12 denotes a hydrogen atom or a methyl radical;

R10 and R11, independently of each other, denote a C1-C6 alkyl group, a C1-C5 hydroxyalkyl group, a C1-04 amidoalkyl group; or alternatively R10 and R11 may denote, together with the nitrogen atom to which they are attached, a heterocyclic group such as piperidyl or morpholinyl; R10 and R11, independently of each other, preferably denote a C1-C4 alkyl group;

Y— is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer for example sold under the name Merquat 100 by the company Nalco and the copolymers of diallyldimethylammonium salt (for example chloride) and of acrylamide, sold in particular under the name Merquat 550 or Merquat 7SPR.

(8) quaternary diammonium polymers comprising repeating units of formula:

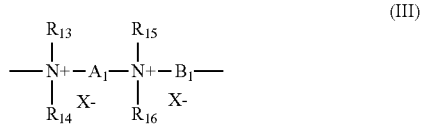

wherein:

R13, R14, R15 and R16, which may be identical or different, represent aliphatic, alicyclic or arylaliphatic radicals comprising from 1 to 20 carbon atoms or C1-C12 hydroxyalkyl aliphatic radicals, or else R13, R14, R15 and R16, together or separately, form, with the nitrogen atoms to which they are attached, heterocycles optionally comprising a second non-nitrogen heteroatom;

or else R13, R14, R15 and R16 represent a linear or branched C1-C6 alkyl radical substituted with a nitrile, ester, acyl, amide or —CO—O—R17-D or —CO—NH—R17-D group, where R17 is an alkylene and D is a quaternary ammonium group;

A1 and B1 represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and X— denotes an anion derived from a mineral or organic acid;

it being understood that A1, R13 and R15 can form, with the two nitrogen atoms to which they are attached, a piperazine ring;

in addition, if A1 denotes a linear or branched, saturated or unsaturated alkylene or hydroxyalkylene radical, B1 may also denote a group (CH2)n-CO-D-OC—(CH2)p- with n and p, which may be identical or different, being integers ranging from 2 to 20, and D denoting:

a) a glycol residue of formula —O—Z—O—, in which Z denotes a linear or branched hydrocarbon-based radical, or a group corresponding to one of the following formulae: —(CH2CH2O)x-CH2CH2- and —[CH2CH(CH3)O]y-CH2CH(CH3)-, in which x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula —NH—Y—NH—, in which Y denotes a linear or branched hydrocarbon-based radical, or else the divalent radical —CH2-CH2-S—S—CH2-CH2-;

d) a ureylene group of formula —NH—CO—NH—.

Preferably, X— is an anion such as chloride or bromide. These polymers have a number-average molar mass (Mn) generally of between 1000 and 100 000.

Mention may be made more particularly of polymers that are composed of repeating units corresponding to the formula:

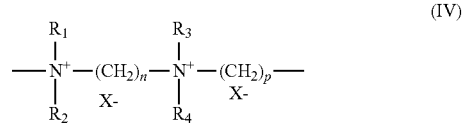

in which R1, R2, R3 and R4, which may be identical or different, denote an alkyl or hydroxyalkyl radical containing from 1 to 4 carbon atoms, n and p are integers ranging from 2 to 20, and X— is an anion derived from a mineral or organic acid.

A particularly preferred compound of formula (IV) is the one for which R1, R2, R3 and R4 represent a methyl radical and n=3, p=6 and X=Cl, known as Hexadimethrine chloride according to the INCI (CTFA) nomenclature.

(9) polyquaternary ammonium polymers comprising units of formula (V):

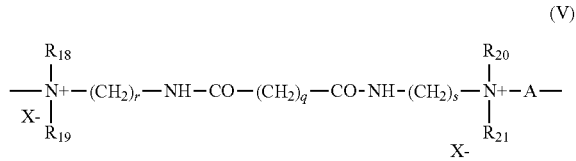

wherein:
R18, R19, R20 and R21, which may be identical or different, represent a hydrogen atom or a methyl, ethyl, propyl, β-hydroxyethyl, β-hydroxypropyl or —CH2CH2(OCH2CH2)pOH radical, in which p is equal to 0 or to an integer between 1 and 6, with the proviso that R18, R19, R20 and R21 do not simultaneously represent a hydrogen atom, r and s, which may be identical or different, are integers between 1 and 6, q is equal to 0 or to an integer between 1 and 34, X— denotes an anion such as a halide, A denotes a divalent dihalide radical or preferably represents —CH2-CH2-O-CH2-CH2-.

Examples that may be mentioned include the products Mirapol® A 15, Mirapol® AD1, Mirapol® AZ1 and Mirapol® 175 sold by the company Miranol.

(10) quaternary polymers of vinylpyrrolidone and of vinylimidazole, for instance the products sold under the names Luviquat® FC 905, FC 550 and FC 370 by the company BASF.

(11) polyamines such as Polyquart® H sold by Cognis, referred to under the name Polyethylene glycol (15) tallow polyamine in the CTFA dictionary.

(12) polymers comprising in their structure:
(a) one or more units corresponding to formula (A) below:

(A)

(b) optionally one or more units corresponding to formula (B) below:

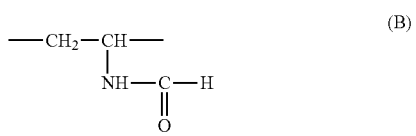

(B)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to the formula (A) and from 0 to 95 mol % of units corresponding to the formula (B), preferably from 10 mol % to 100 mol % of units corresponding to the formula (A) and from 0 to 90 mol % of units corresponding to the formula (B).

These polymers may be obtained, for example, by partial hydrolysis of polyvinylformamide. This hydrolysis may take place in acidic or basic medium.

The weight-average molecular mass of said polymer, measured by light scattering, may range from 1000 to 3 000 000 g/mol, preferably from 10 000 to 1 000 000 and more particularly from 100 000 to 500 000 g/mol.

The polymers comprising units of formula (A) and optionally units of formula (B) are sold in particular under the Lupamin name by BASF, for instance, in a non-limiting way, the products provided under the names Lupamin 9095, Lupamin 5095, Lupamin 1095, Lupamin 9030 (or Luviquat 9030) and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the cationic polymers are chosen from those of families (1), (2), (7), (8) and (10) mentioned above, and more preferentially from those of families (1), (2) and (8).

More preferably, use is made of a cationic polymer chosen from polymers, which are preferably crosslinked, of methacryloyloxy(C1-C4)alkyltri(C1-C4)alkylammonium salts, dialkyldiallylammonium halide homopolymers, more particularly the dialkyldiallylammonium chloride homopolymer (INCI name: Polyquaternium-6), quaternary diammonium polymers, more particularly Hexadimethrine chloride according to the INCI nomenclature.

Use may also be made, for example, of a crosslinked methacryloyloxyethyltrimethylammonium chloride homopolymer comprising about 50% by weight of the homopolymer in mineral oil or in a liquid ester, sold under the name Salcare® SC 95 by the company Ciba. Use may also be made of the dialkyldiallylammonium chloride homopolymer (INCI name: Polyquaternium-6) sold under the name Merquat® 100 by the company Nalco. Use may also be made of the hexadimethrine chloride sold under the name Mexomer PO by the company Chimex.

When they are present, the cationic polymers may be present in an amount ranging from 0.01% to 15% by weight, preferably from 0.05% to 10% by weight and better still from 0.075% to 5% by weight, relative to the total weight of the composition.

The composition used in the process according to the invention may also comprise one or more silicones, which may be solid or liquid, volatile or non-volatile, and amino or non-amino.

As silicones that may be used, mention may be made, alone or as a mixture, of polydialkylsiloxanes and especially polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes comprising in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, especially polydiphenylsiloxanes, and polyalkylarylsiloxanes, functionalized with the organofunctional groups mentioned previously.

Among the organomodified silicones, mention may be made of organopolysiloxanes comprising:
polyoxyethylene and/or polyoxypropylene groups optionally comprising C6-C24 alkyl groups, such as dimethicone copolyols, and especially those sold by the company Dow Corning under the name DC 1248 or the oils Silwet® L 722, L 7500, L 77 and L 711 from the company Union Carbide; or alternatively (C12)alkylmethicone copolyols, and especially those sold by the company Dow Corning under the name Q2 5200;
substituted or unsubstituted amine groups, in particular C1-C4 aminoalkyl groups; mention may be made of the products sold under the name GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in patent U.S. Pat. No. 4,957,732;

anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

The polydialkylsiloxanes may be chosen mainly from polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, such as, for example, the oil 70 047 V 500 000;

the oils of the Mirasil® series sold by the company Rhodia;

the oils of the 200 series from Dow Corning, such as DC200, with a viscosity of 60 000 mm²/s;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning.

The polyalkylarylsiloxanes are chosen particularly from linear and/or branched polydimethyl/methylphenylsiloxanes and polydimethyl/diphenylsiloxanes preferably with a viscosity ranging from $1 \times 10^{-5}$ to $5 \times 10^{-2}$ m²/s at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Preferably, the composition according to the invention comprises one or more amino silicones.

For the purposes of the present invention, the term "amino silicone" means any silicone comprising one or more primary, secondary or tertiary amine functions or one or more quaternary ammonium groups.

The amino silicones that may be used in the cosmetic composition according to the present invention are advantageously chosen, alone or as a mixture, from:

a) amino silicones containing one or more primary amine functions, and especially those of formula (II') and b) amino silicones containing one or more non-amidated quaternized amine functions, and especially those of formulae (III') and (IV').

According to the present invention, the term "non-amidated silicone" means a silicone that does not comprise any amide functions (—NHC(O)—).

The composition according to the invention may especially comprise one or more amino silicones containing one or more primary amine functions, and corresponding to formula (II'):

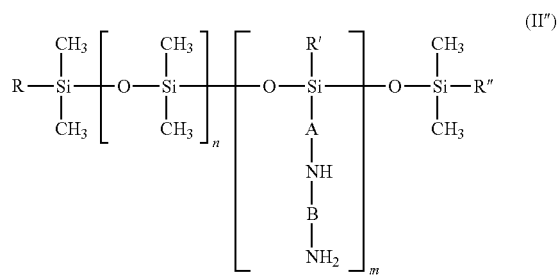

in which:

R, R' and R", which may be identical or different, denote a C1-C4 alkyl radical, preferably CH3; a C1-C4 alkoxy radical, preferably methoxy; or OH; with the proviso that R and R" do not simultaneously denote OH, A and B represent, independently of each other, a linear or branched C2-C8 alkylene radical; A preferably represents a C3-C6 alkylene; B preferably represents a C2-C4 alkylene;

m and n are integers that are dependent on the molecular weight (Mw) of the silicone, and whose sum ranges from 1 to 2000.

According to a first variant of formula (II'), R, R' and R", which may be identical or different, represent a C1-C4 alkoxy radical or a hydroxyl radical, at least one of the radicals R or R" being a C1-C4 alkoxy radical; A represents a C3 alkylene radical and B represents a C2-C4 alkylene radical.

The hydroxyl/alkoxy mole ratio is preferably between 0.2/1 and 0.4/1 and advantageously equal to 0.3/1. Moreover, m and n are such that the weight-average molecular mass (Mw) of the silicone is between 2000 and $10^6$. More particularly, n is between 0 and 999 and m is between 1 and 1000, the sum of n and m being between 1 and 1000.

A commercial product that may be mentioned is the product Belsil® ADM 652 sold by Wacker.

According to a second variant of formula (II'), R and R", which are different, represent a C1-C4 alkoxy radical or a hydroxyl radical, at least one of the radicals R or R" being a C1-C4 alkoxy radical; R' represents a methyl radical, A represents a C3 alkylene radical and B represents a C2-C4 alkylene radical.

The hydroxyl/alkoxy mole ratio is preferably between 1/0.8 and 1/1.1 and advantageously is equal to 1/0.95. Moreover, m and n are such that the weight-average molecular mass (Mw) of the silicone is between 2000 and 200 000. More particularly, n is between 0 and 999 and m is between 1 and 1000, the sum of n and m being between 1 and 1000.

A commercial product that may be mentioned is the product FluidWR® 1300 sold by Wacker.

According to a third variant of formula (II'), R, R" and R' represent a methyl radical, A represents a C4 alkylene radical and B represents a C2-C4 alkylene radical; m and n being integers that are dependent on the molecular weight (Mw) of the silicone, and the sum of which ranges from 1 to 2000.

in which:
R5, which may be identical or different, represent a linear or branched C1-C18 alkyl radical or a linear or branched C2-C18 alkenyl radical; preferably a methyl radical;
R6 represents a linear or branched C1-018 divalent alkylene radical or a linear or branched C1-018, for example C1-08, divalent alkylenoxy radical linked to the Si via an SiC bond;
Q- is an anion such as a halide ion, especially chloride, or an organic acid salt (for example acetate);
r represents a mean statistical value and ranges from 2 to 20 and in particular from 2 to 8;
s represents a mean statistical value and ranges from 20 to 200 and in particular from 20 to 50;
2) the quaternary ammonium silicones of formula:

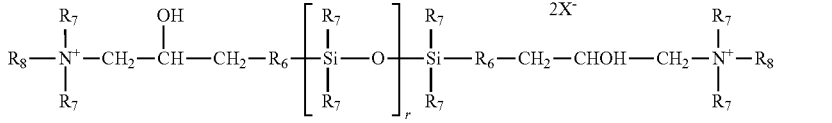

A silicone that is particularly preferred according to this variant is the polymer known in the CTFA dictionary as "trimethylsilyl amodimethicone", corresponding to the following formula:

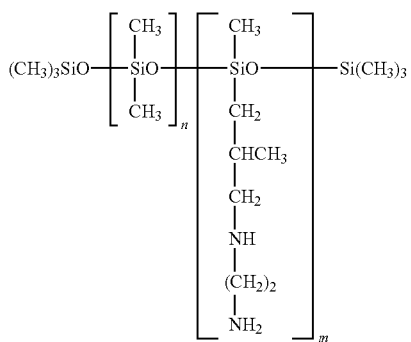

in which m and n are integers that are dependent on the molecular weight (Mw) of the silicone, and whose sum ranges from 1 to 2000.

A commercial product that may be mentioned is the product sold under the name Q2-8220 by the company OSI.

The composition according to the invention may especially comprise one or more amino silicones containing one or more non-amidated quaternized amine functions, and corresponding to formula (III') or (IV'):

1) the quaternary ammonium silicones of formula:

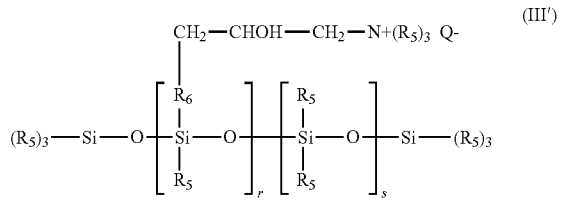

in which:
R7, which may be identical or different, represent a linear or branched C1-C18 alkyl radical or a linear or branched C2-C18 alkenyl radical or a hydrocarbon-based ring comprising 5 or 6 carbon atoms; preferably a methyl radical;
R6, which may be identical or different, represent a linear or branched C1-018 divalent alkylene radical or a linear or branched C1-018, for example C1-08, divalent alkylenoxy radical linked to the Si via an SiC bond;
R8, which may be identical or different, represent a hydrogen atom, a linear or branched C1-C18 alkyl radical or a linear or branched C2-C18 alkenyl radical;
X— is an anion such as a halide ion, especially chloride, or an organic acid salt (for example acetate);
r represents a mean statistical value and ranges from 2 to 200 and in particular from 5 to 100.

Preferably, the composition according to the invention comprises at least one silicone of formula (IV') in which all the R7 are methyl radicals and the R6 are both 01-08 and especially C2-C4 alkylenoxy.

In particular, mention may be made of the silicone having the INCI name: Quaternium-80.

A commercial product that may be mentioned is the product sold under the name Abil Quat 3272 or 3274 by the company Degussa.

The weight-average molecular mass (Mw) of these silicones may advantageously be determined by gel permeation chromatography (room temperature 25° C., polystyrene standard, μ styragem columns, THF eluent, flow rate of 1 mm/minute, 200 μl of a solution containing 0.5% by weight of silicone in THF are injected, and detection is performed by refractometry and UV-metry).

According to the invention, all these silicones may also be used in the form of emulsions or microemulsions.

When they are present, the silicones are present in an amount ranging from 0.01% to 10% by weight, preferably from 0.05% to 5% by weight and preferentially from 0.1% to 2% by weight, relative to the total weight of the composition.

Non-Silicone Fatty Substances

The composition used in the process according to the invention may comprise one or more non-silicone fatty substances other than the plant waxes as described previously.

The term "fatty substance" means an organic compound that is insoluble in water at room temperature (25° C.) and at atmospheric pressure (1 atm), i.e. which has a solubility of less than 5% by weight, preferably less than 1% by weight. They are generally soluble, under the same temperature and pressure conditions, in organic solvents such as chloroform, ethanol, benzene, liquid petroleum jelly or decamethylcyclopentasiloxane.

The term "non-silicone fatty substance" means a fatty substance whose structure does not comprise any silicon atoms, and which therefore especially does not comprise any siloxane groups. They generally bear in their structure a hydrocarbon-based chain comprising at least 6 carbon atoms. Advantageously, they are not oxyalkylenated and do not contain any —COOH functions.

The fatty substance(s) may be chosen from solid fatty substances and/or liquid fatty substances (also called "oil"), and mixtures thereof.

The term "oil" means a "fatty substance" which is liquid, i.e. which is capable of flowing under the action of its own weight at room temperature (25° C.) and at atmospheric pressure (760 mmHg, i.e. $1.013 \times 10^5$ Pa). Preferably, the viscosity at a temperature of 25° C. and at a shear rate of 1 $s^{-1}$ of the oil is between $10^{-3}$ Pa·s and 2 Pa·s. It may be measured using a Thermo Haake RS600 rheometer with cone-plate geometry or an equivalent machine.

The non-silicone liquid fatty substances that may be used in the composition according to the invention are chosen from hydrocarbons, fatty alcohols, fatty acid and/or fatty alcohol esters, and non-salified fatty acids.

The term "liquid hydrocarbon" means a hydrocarbon composed solely of carbon and hydrogen atoms, which is liquid at standard temperature (25° C.) and at atmospheric pressure (760 mmHg, i.e. $1.013 \times 10^5$ Pa).

More particularly, the liquid hydrocarbons that may be used in the composition according to the invention are chosen from:
- linear or branched, optionally cyclic, $C_6$-$C_{16}$ alkanes. Examples that may be mentioned include hexane, undecane, dodecane, tridecane, and isoparaffins, for instance isohexadecane, isododecane and isodecane,
- linear or branched hydrocarbons of synthetic, animal or mineral origin, of more than 16 carbon atoms, such as liquid paraffin or liquid petroleum jelly, polydecenes, hydrogenated polyisobutene such as the product sold under the brand name Parleam® by the company NOF Corporation, and squalane.

Preferably, the liquid hydrocarbon(s) are chosen from liquid paraffins, isoparaffins, liquid petroleum jelly, undecane, tridecane and isododecane, and mixtures thereof.

In a most particularly preferred variant, the liquid hydrocarbon(s) are chosen from liquid paraffin, liquid petroleum jelly, isoparaffins, isododecane and a mixture of undecane and tridecane.

The term "liquid fatty alcohol" means a non-glycerolated and non-oxyalkylenated fatty alcohol, which is liquid at standard temperature (25° C.) and at atmospheric pressure (760 mmHg, i.e. $1.013 \times 10^5$ Pa). Preferably, the liquid fatty alcohols that may be used in the composition according to the invention comprise from 8 to 30 carbon atoms and may be saturated or unsaturated.

The saturated liquid fatty alcohols are preferably branched. They may optionally comprise in their structure at least one aromatic or non-aromatic ring. Preferably, they are acyclic.

More particularly, the saturated liquid fatty alcohols that may be used in the composition according to the invention are chosen from octyldodecanol, 2-decyltetradecanol, isostearyl alcohol and 2-hexyldecanol.

Octyldodecanol and 2-decyltetradecanol are most particularly preferred.

The unsaturated liquid fatty alcohols contain in their structure at least one double or triple bond, and preferably one or more double bonds. When several double bonds are present, there are preferably 2 or 3 of them, and they may be conjugated or unconjugated.

These unsaturated fatty alcohols may be linear or branched.

They may optionally comprise in their structure at least one aromatic or non-aromatic ring. They are preferably acyclic.

More particularly, the unsaturated liquid fatty alcohols that may be used in the composition according to the invention are chosen from oleyl alcohol, linoleyl alcohol, linolenyl alcohol and undecylenyl alcohol.

Oleyl alcohol is most particularly preferred.

The term "liquid fatty ester" means an ester derived from a fatty acid and/or from a fatty alcohol, which is liquid at normal temperature (25° C.) and at atmospheric pressure (760 mmHg; i.e. $1.013 \times 10^5$ Pa).

More particularly, the liquid esters are chosen from saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbon atoms in the esters being greater than or equal to 10.

For the esters of monoalcohols, preferably at least one from among the alcohol and the acid from which the esters of the invention are obtained is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may be used.

Mention may be made in particular of diethyl sebacate, diisopropyl sebacate, diisopropyl adipate, di-n-propyl adipate, dioctyl adipate, diisostearyl adipate, dioctyl maleate, glyceryl undecylenate, octyldodecyl stearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate, propylene glycol dicaprate, tridecyl erucate, triisopropyl citrate, triisostearyl citrate, glyceryl trilactate, glyceryl trioctanoate, trioctyldodecyl citrate, trioleyl citrate, propylene glycol dioctanoate, neopentyl glycol diheptanoate, diethylene glycol diisononanoate and polyethylene glycol distearates.

Among the esters mentioned above, use is preferentially made of ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

Among the liquid fatty esters, use may be made of sugar esters and diesters of $C_6$-$C_{30}$ and preferably $C_{12}$-$C_{22}$ fatty acids.

The term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Preferably, these said sugars are chosen from saccharose, glucose, galactose, ribose, fucose, maltose, fructose, mannose, arabinose, xylose and lactose, and derivatives thereof, especially alkyl derivatives, such as methyl derivatives, for instance methylglucose.

The sugar and fatty acid esters may be chosen in particular from the group comprising the esters or mixtures of esters of sugars described previously and of linear or branched, saturated or unsaturated $C_6$-$C_{30}$ and preferably $C_{12}$-$C_{22}$ fatty acids.

If they are unsaturated, these compounds may have one to three conjugated or unconjugated carbon-carbon double bonds.

The esters according to this variant may also be chosen from mono-, di-, tri- and tetraesters, and polyesters, and mixtures thereof.

These said esters may be, for example, oleates, laurates, palmitates, myristates, behenates, cocoates, stearates, linoleates, linolenates, caprates and arachidonates, or mixtures thereof, such as, in particular, oleopalmitate, oleostearate or palmitostearate mixed esters.

More particularly, use is made of monoesters and diesters and especially of sucrose, glucose or methylglucose mono- or dioleates, stearates, behenates, oleopalmitates, linoleates, linolenates or oleostearates, or alternatively of methylglucose dioleate (Glucate® DO).

Among the sugar esters, use may be made of pentaerythrityl esters, preferably pentaerythrityl tetraisostearate, pentaerythrityl tetraoctanoate, and caprylic and capric acid hexaesters as a mixture with dipentaerythritol.

Among the natural or synthetic monoacid, diacid or triacid esters of glycerol, use may be made of plant oils or synthetic oils.

More particularly, said plant oil(s) or synthetic oil(s) are chosen from triglyceride oils of plant or synthetic origin, such as liquid fatty acid triglycerides containing from 6 to 30 carbon atoms, for instance heptanoic or octanoic acid triglycerides, or alternatively, for example, sesame oil, wheatgerm oil, soybean oil, coffee oil, safflower oil, borage oil, sunflower oil, olive oil, apricot kernel oil, *camellia* oil, bambara pea oil, avocado oil, mango oil, rice bran oil, cotton seed oil, rose oil, kiwi seed oil, sea buckthorn pulp oil, blueberry seed oil, poppy seed oil, orange pip oil, sweet almond oil, castor oil, coconut oil, *vernonia* oil, marjoram oil, baobab oil, rapeseed oil, ximenia oil, pracaxi oil, caprylic/capric acid triglycerides such as those sold by the company Stéarineries Dubois or those sold under the names Miglyol® 810, 812 and 818 by the company Dynamit Nobel, jojoba oil and shea butter oil.

As liquid esters that may be used according to the invention, use is preferably made of triglycerides of plant origin, in particular oils chosen from avocado oil, olive oil, *camellia* oil, apricot kernel oil and castor oil, and mixtures thereof, and $C_4$-$C_{22}$ dicarboxylic or tricarboxylic acid esters of $C_1$-$C_{22}$ alcohols, in particular 1,3-propanediol dicaprylate.

The term "fatty acid" means a non-salified fatty acid, i.e. the fatty acid must not be in the form of a generally soluble soap, i.e. it must not be salified with a base.

More particularly, the liquid fatty acids according to the invention are chosen from the acids of formula RCOOH, in which R is a saturated or unsaturated, linear or branched radical preferably comprising from 7 to 39 carbon atoms.

Preferably, R is a $C_7$-$C_{29}$ alkyl or $C_7$-$C_{29}$ alkenyl group and better still a $C_{12}$-$C_{24}$ alkyl or $C_{12}$-$C_{24}$ alkenyl group. R may be substituted with one or more hydroxyl groups and/or one or more carboxyl groups.

Preferentially, the liquid fatty acid(s) are chosen from oleic acid, linoleic acid and isostearic acid.

Preferentially, the non-silicone liquid fatty substance(s) that may be used in the composition used in the process according to the invention are chosen from plant oils and mineral oils.

More preferentially, the non-silicone liquid fatty substance(s) are chosen from castor oil, wheatgerm oil and liquid paraffin.

For the purposes of the present invention, the term "solid fatty substance" means a fatty substance that is not liquid at room temperature (25° C.) and atmospheric pressure (760 mmHg, i.e. $1.013 \times 10^5$ Pa), in particular a solid compound or a compound with a viscosity of greater than 2 Pa·s at a shear rate of $1\ s^{-1}$ under the conditions mentioned above.

The solid fatty substances used in the composition according to the invention have a melting point above room temperature, preferably a melting point greater than or equal to 30° C., preferentially greater than or equal to 40° C., preferentially ranging from 46 to 95° C.

The solid non-silicone fatty substances that may be used in the context of the invention may be chosen from fatty alcohols, esters of a fatty acid and/or of a fatty alcohol, non-silicone waxes, ceramides, and mixtures thereof.

The term "fatty alcohol" means a long-chain aliphatic alcohol comprising from 8 to 40 carbon atoms and comprising at least one hydroxyl group OH. These fatty alcohols are neither oxyalkylenated nor glycerolated.

The solid fatty alcohols may be saturated or unsaturated, and linear or branched, and comprise from 8 to 40 carbon atoms. Preferably, the solid fatty alcohols have the structure R—OH with R denoting a linear alkyl group, optionally substituted with one or more hydroxyl groups, comprising from 8 to 40, better still from 10 to 30, or even from 12 to 24 and even better still from 14 to 22 carbon atoms.

The solid fatty alcohols that can be used are preferably chosen from saturated or unsaturated, linear or branched, preferably linear and saturated, (mono)alcohols comprising from 8 to 40 carbon atoms, better still from 10 to 30, or even from 12 to 24 atoms and better still from 14 to 22 carbon atoms.

The solid fatty alcohols that can be used may be chosen from, alone or as a mixture:
  lauryl alcohol (or 1-dodecanol);
  myristyl alcohol (or 1-tetradecanol);
  cetyl alcohol (or 1-hexadecanol);
  stearyl alcohol (or 1-octadecanol);
  arachidyl alcohol (or 1-eicosanol);
  behenyl alcohol (or 1-docosanol);
  lignoceryl alcohol (or 1-tetracosanol);
  ceryl alcohol (or 1-hexacosanol);
  montanyl alcohol (or 1-octacosanol);
  myricyl alcohol (or 1-triacontanol).

Preferentially, the solid fatty alcohol is chosen from cetyl alcohol, stearyl alcohol, behenyl alcohol, myristyl alcohol, and mixtures thereof, such as cetylstearyl alcohol or cetearyl alcohol.

The solid esters of a fatty acid and/or of a fatty alcohol that may be used are preferably chosen from esters derived from a C9-C26 carboxylic fatty acid and/or from a C9-C26 fatty alcohol.

Preferably, these solid fatty esters are esters of a linear or branched, saturated carboxylic acid comprising at least 10 carbon atoms, preferably from 10 to 30 carbon atoms and more particularly from 12 to 24 carbon atoms, and of a linear or branched, saturated monoalkyl, comprising at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of C4-C22 dicarboxylic or tricarboxylic acids and of C1-022 alcohols and esters of monocarboxylic, dicarboxylic or tricarboxylic acids and of C2-C26 dihydroxy, trihydroxy, tetrahydroxy or pentahydroxy alcohols may also be used.

Mention may in particular be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from C9-C26 alkyl palmitates, in particular myristyl, cetyl or stearyl palmitate; C9-C26 alkyl myristates, such as cetyl myristate, stearyl myristate and myristyl myristate; and C9-C26 alkyl stearates, in particular myristyl stearate, cetyl stearate and stearyl stearate; and mixtures thereof.

For the purposes of the present invention, a wax is a lipophilic compound, which is solid at room temperature (25° C.) and atmospheric pressure, with a reversible solid/liquid change of state, having a melting point greater than about 30° C., preferentially greater than about 40° C., which may be up to 200° C., and having in the solid state an anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but if the temperature of the mixture is brought back to room temperature, recrystallization of the wax, which is microscopically and macroscopically detectable (opalescence), is obtained.

In particular, the waxes that are suitable for use in the invention may be chosen from waxes of animal or mineral origin, non-silicone synthetic waxes, and mixtures thereof.

Mention may be made especially of hydrocarbon-based waxes, for instance beeswax, in particular of biological origin, lanolin wax and Chinese insect waxes; shellac wax, microcrystalline waxes, paraffins and ozokerite; polyethylene waxes, the waxes obtained by Fisher-Tropsch synthesis and waxy copolymers, and also esters thereof.

Mention may thus be made of C2 to C60 microcrystalline waxes, such as Microwax HW.

Mention may also be made of the PM 500 polyethylene wax sold under the reference Permalen 50-L polyethylene.

Mention may also be made of the waxes obtained by catalytic hydrogenation of animal oils. Among these, mention may be made especially of hydrogenated lanolin oil, and bis(1,1,1-trimethylolpropane) tetrastearate, especially the product sold under the name Hest 2T-4S® by the company Heterene.

A wax that may also be used is a C20-C40 alkyl (hydroxystearyloxy)stearate (the alkyl group containing from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

It is also possible to use microwaxes in the compositions; mention may be made especially of microwaxes of synthetic wax, such as the product sold under the name MicroEase 1145® by the company Micro Powders, polyethylene microwaxes, such as those sold under the names Micropoly 200®, 220®, 220L® and 2505® by the company Micro Powders, and polytetrafluoroethylene microwaxes, such as those sold under the names Microslip 519® and 519 L® by the company Micro Powders.

The waxes are preferably chosen from mineral waxes, for instance paraffin wax, petroleum jelly wax, lignite wax or ozokerite; waxes of animal origin, for instance beeswaxes or modified beeswaxes (cerabellina), spermaceti, lanolin wax and lanolin derivatives; microcrystalline waxes; and mixtures thereof.

The ceramides, or ceramide analogues such as glycoceramides, that may be used in the compositions according to the invention, are known; mention may in particular be made of ceramides of classes I, II, III and V according to the Dawning classification.

The ceramides or analogues thereof that may be used preferably correspond to the following formula:

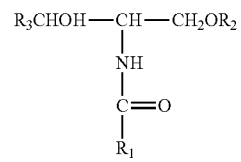

in which:
R1 denotes a linear or branched, saturated or unsaturated alkyl group, derived from C14-C30 fatty acids, it being possible for this group to be substituted with a hydroxyl group in the alpha position, or a hydroxyl group in the omega position esterified with a saturated or unsaturated C16-C30 fatty acid;
R2 denotes a hydrogen atom or a (glycosyl)n group, a (galactosyl)m group or a sulfogalactosyl group, in which n is an integer ranging from 1 to 4 and m is an integer ranging from 1 to 8;
R3 denotes a C15-C26 hydrocarbon-based group which is saturated or unsaturated in the alpha position, it being possible for this group to be substituted with one or more C1-C14 alkyl groups;
it being understood that, in the case of natural ceramides or glycoceramides, R3 can also denote a C15-C26 α-hydroxyalkyl group, the hydroxyl group being optionally esterified with a C16-C30 α-hydroxy acid.

The ceramides that are more particularly preferred are the compounds for which R1 denotes a saturated or unsaturated alkyl derived from C16-C22 fatty acids; R2 denotes a hydrogen atom; and R3 denotes a saturated linear C15 group.

Preferentially, ceramides are used for which R1 denotes a saturated or unsaturated alkyl group derived from C14-C30 fatty acids; R2 denotes a galactosyl or sulfogalactosyl group; and R3 denotes a —CH=CH—(CH2)12-CH3 group.

Use may also be made of the compounds for which R1 denotes a saturated or unsaturated alkyl radical derived from C12-C22 fatty acids; R2 denotes a galactosyl or sulfogalactosyl radical and R3 denotes a saturated or unsaturated C12-C22 hydrocarbon-based radical and preferably a —CH=CH—(CH2)12-CH3 group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4 triol and in particular N-stearoylphytosphingosine; 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-Oleoyldihydrosphingosine will preferably be used.

Preferentially, the solid non-silicone fatty substance(s) that may be used in the composition used in the process according to the invention are chosen from solid fatty alcohols, solid fatty esters, particularly from C9-C26 alkyl palmitates and C9-C26 alkyl stearates.

More preferentially, the solid non-silicone fatty substance(s) are chosen from cetylstearyl or cetearyl alcohol, myristyl palmitates and myristyl stearates, and mixtures thereof.

Preferably, the composition according to the invention comprises one or more non-silicone fatty substances other than plant waxes, chosen from plant oils, especially castor oil, wheat germ oil, liquid paraffins, solid fatty esters and solid fatty alcohols, and more preferably from cetylstearyl or cetearyl alcohol, myristyl palmitates and myristyl stearates, and mixtures thereof.

When it comprises them, the composition comprises one or more non-silicone fatty substances other than plant waxes, in an amount ranging from 0.1% to 20% by weight, preferably from 0.5% to 15% by weight and preferentially from 1% to 12% by weight relative to the total weight of the composition.

The composition used in the process according to the invention is aqueous. It comprises at least 60% by weight of water, relative to the total weight of the composition.

Preferably, the composition comprises a weight amount of water ranging from 60% to 95%, preferably from 65% to 90% and more preferably from 70% to 85% relative to the total weight of the composition.

The composition may also contain other active agents, especially organic acids other than fatty acids, amino acids, sunscreens, polymers other than the cationic polymers, organic or mineral thickeners, antioxidants, penetrants, sequestrants, fragrances, buffers, dispersants, film-forming agents, preserving agents, stabilizers and opacifiers.

Needless to say, a person skilled in the art will take care to select this or these optional additional compound(s) such that the advantageous properties intrinsically associated with the composition in accordance with the invention are not, or are not substantially, adversely affected by the envisaged addition(s).

Preferably, the composition used in the process of the invention does not comprise any reducing agent.

According to the present invention, the term "reducing agent" means an agent that is capable of reducing the disulfide bonds of the hair, such as compounds chosen from thiols, alkaline sulfites, hydrides and phosphines.

The composition used in the process according to the invention may be in the form of a gel, a hair lotion or a cream. Preferably, the composition is in the form of a cream.

After applying the composition that has just been described to keratin fibres such as the hair, the process according to the invention comprises a step of heating the keratin fibres by means of a heating appliance which is moved along the fibres.

Preferably, the heating appliance is moved along the keratin fibres, directly after the step of applying the composition to the fibres. In other words, no rinsing step is envisaged between the application of the composition to the keratin fibres and the heating step.

The heating appliance is preferably moved along the keratin fibres from the root to the end.

When the heating appliance is moved along the keratin fibres, it heats to a temperature ranging from 80° C. to 160° C. Preferably, it heats to a temperature ranging from 110° C. to 150° C. and more preferably from 120° C. to 150° C.

According to a preferred embodiment, the heating appliance is a flat iron comprising two arms that are mobile between a closed-together configuration for treating the keratin fibres and an opened-apart configuration.

Preferably, at least one of the arms comprises at least one plate for treating the keratin fibres, configured to heat up, and more preferably both arms comprise at least one plate for treating the keratin fibres.

According to a particularly preferred embodiment, at least one of the treatment plates is equipped with a seal. More preferably, both the treatment plates are equipped with a seal.

Such a flat iron has the advantage of being waterproof.

The heating appliance that may be used in the process according to the invention may be a flat iron such as that described in patent application WO 2015/091 043, which is incorporated herein by reference.

The process then optionally comprises a step of rinsing or washing the keratin fibres after the heating step, generally with water or with shampoo, optionally followed by a drying step and optionally a styling step.

EXAMPLE

The following care composition was prepared (in mass percentages of active material):

| Composition | 1 |
| --- | --- |
| Cetylstearyl alcohol (50/50 C16/018) | 4.00 |
| Myristyl palmitate/stearate mixture | 1.00 |
| Wheatgerm oil | 2.00 |
| Candelilla wax | 0.75 |
| Beeswax | 0.15 |
| Palm oil | 3.00 |
| Behenyltrimethylammonium chloride | 4.93 |
| Trideceth-6 | 0.07 |
| Mineral oil | 0.05 |
| Polyquaternium-37 | 0.07 |
| Cetyltrimethylammonium chloride | 0.01 |
| Isopropyl alcohol | 1.12 |

-continued

| Composition | 1 |
| --- | --- |
| Amodimethicone | 0.86 |
| Pentaerythrityl tetrakis(di-t-butyl) hydroxyhydrocinnamate | 0.10 |
| Fragrance | 0.30 |
| Preserving agents | 0.54 |
| Water | qs 100 |

The process according to the invention was performed on a panel of 50 women having dry/damaged, dyed, mid-length (shoulder-length) to long hair.

In a first stage, the women's hair was washed and towel-dried carefully to remove the excess moisture. It was then disentangled using a brush or a comb.

Composition 1 was then applied to the hair, at a rate of 14 g per head.

The hair was then combed using a comb so as to distribute the composition over the hair.

A flat iron such as that described in patent application WO 2015/091 043 was then moved over the entire length of the hairs, the iron heating at a temperature of 140° C., via two passes of the iron over the entire head of hair.

The hair was then rinsed and dried using a hairdryer, performing blow-drying.

Immediately after this treatment, the women evaluated their hair.

- 94% of the women of the panel estimated that their hair was nourished;
- 92% of the women of the panel estimated that their hair was less damaged;
- 92% of the women of the panel estimated that their hair was smoother;
- 96% of the women of the panel estimated that their hair was more conditioned;
- 96% of the women of the panel estimated that their hair was softer;
- 78% of the women of the panel estimated that their hair was shinier;
- 90% of the women of the panel estimated that the ends of their hair appeared to be managed;
- 90% of the women of the panel estimated that they were less frizzy.

After three shampoo washes, the women evaluated their hair again:

- 86% of the women of the panel estimated that their hair was nourished;
- 76% of the women of the panel estimated that their hair was less damaged;
- 86% of the women of the panel estimated that their hair was smoother;
- 88% of the women of the panel estimated that their hair was more conditioned;
- 90% of the women of the panel estimated that their hair was softer;
- 74% of the women of the panel estimated that their hair was shinier;
- 72% of the women of the panel estimated that the ends of their hair appeared to be managed;
- 82% of the women of the panel estimated that they were less frizzy;
- 74% of the women of the panel estimated that their hair was easier to disentangle.

Finally, after six shampoo washes, the women evaluated their hair again:

- 66% of the women of the panel estimated that their hair was nourished;
- 76% of the women of the panel estimated that their hair was less damaged;
- 72% of the women of the panel estimated that their hair was smoother;
- 76% of the women of the panel estimated that their hair was more conditioned;
- 68% of the women of the panel estimated that their hair was softer;
- 58% of the women of the panel estimated that their hair was shinier;
- 62% of the women of the panel estimated that the ends of their hair appeared to be managed;
- 68% of the women of the panel estimated that they were less frizzy;
- 64% of the women of the panel estimated that their hair was easier to disentangle.

The invention claimed is:

1. A process for conditioning keratin fibres comprising:
   i) applying to the keratin fibres a composition comprising:
      at least one plant wax present in the composition in a content ranging from about 0.5% to about 15% by weight, relative to the total weight of the composition,
      at least one oil present in the composition in a content ranging from about 2% to about 20% by weight, relative to the total weight of the composition, and
      water, wherein the water is present in the composition in an amount that is at least 60% by weight, relative to the total weight of the composition;
      wherein the amount of the at least one oil in the composition is greater than the amount of the at least one plant wax in the composition;
   ii) heating the keratin fibres with a heating appliance having a temperature ranging from about 80° C. to about 160° C.; and
   iii) washing or rinsing the keratin fibres.

2. The process according to claim 1, wherein the temperature of the heating appliance ranges from about 120° C. to about 150° C.

3. The process according to claim 1, wherein the at least one plant wax is chosen from carnauba wax, candelilla wax, alfalfa wax, jojoba wax, mimosa wax, rice wax, soybean wax, orange blossom wax, jasmine wax, rose wax, olive wax, ouricury wax, Berry wax, sumac wax, orange wax, lemon wax, cocoa butter, palm butter, cork fibre wax or sugarcane wax, sunflower seed wax, absolute waxes of flowers, or hydrogenated castor oil.

4. The process according to claim 1, wherein the at least one plant wax is chosen from jojoba wax, carnauba wax, candelilla wax, or palm butter.

5. The process according to claim 1, wherein the at least one plant wax is chosen from candelilla wax or jojoba wax.

6. The process according to claim 1, wherein the water is present in the composition in an amount ranging from about 60% to about 95% by weight, relative to the total weight of the composition.

7. The process according to claim 1, wherein the water is present in the composition in an amount ranging from about 70% to about 85% by weight, relative to the total weight of the composition.

8. The process according to claim 1, wherein the composition comprises at least one conditioning agent other than plant waxes and oils, chosen from cationic surfactants, cationic polymers, or silicones.

9. The process according to claim 8, comprising at least one cationic surfactant chosen from those corresponding to the general formula (A1) below:

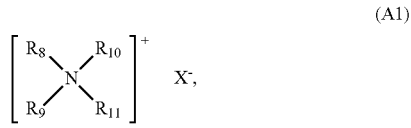

wherein the groups $R_8$ to $R_{11}$, which may be identical or different, represent a linear or branched aliphatic group comprising from 1 to 30 carbon atoms, or an aromatic group, at least one of the groups $R_8$ to $R_{11}$ comprising from 8 to 30 carbon atoms; and $X^-$ is an anion chosen from halides, phosphates, acetates, lactates, $(C_1-C_4)$ alkyl sulfates, or $(C_1-C_4)$alkyl- or $(C_1-C_4)$alkylarylsulfonates.

10. The process according to claim 8, comprising at least one cationic polymer chosen from:
(1) homopolymers or copolymers derived from acrylic or methacrylic esters or amides and comprising at least one of the units of the following formulae:

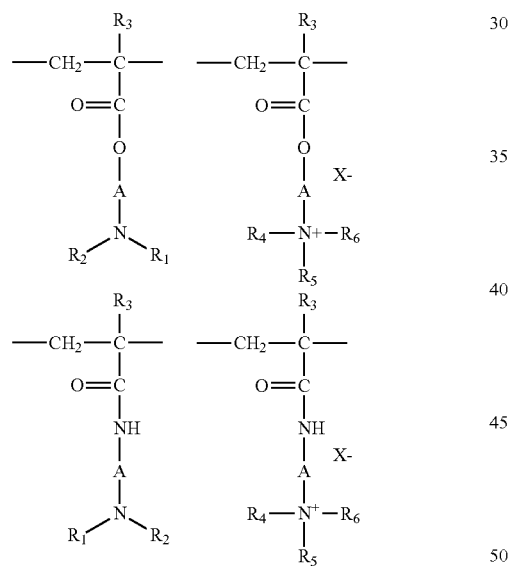

wherein:
R3, which may be identical or different, denote a hydrogen atom or a CH3 radical;
A, which may be identical or different, represents a linear or branched divalent alkyl group of 1 to 6 carbon atoms or a hydroxyalkyl group of 1 to 4 carbon atoms;
R4, R5 and R6, which may be identical or different, represent an alkyl group containing from 1 to 18 carbon atoms or a benzyl radical;
R1 and R2, which may be identical or different, represent a hydrogen atom or an alkyl group containing from 1 to 6 carbon atoms;
X denotes an anion derived from a mineral acid, organic acid, or a halide;

(2) cationic polysaccharides;
(3) polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers;
(4) water-soluble polyaminoamides, wherein the polyaminoamides may be crosslinked:
with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or
with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; wherein the polyaminoamides are optionally alkylated or, if they comprise one or more tertiary amine functions, quaternized;
(5) polyaminoamide derivatives;
(6) polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid being between 0.8:1 and 1.4:1; the resulting polyamino amide being reacted with epichlorohydrin in a mole ratio of epichlorohydrin relative to the secondary amine group of the polyaminoamide;
(7) alkyldiallylamine or dialkyldiallylammonium cyclopolymers comprising units corresponding to formula (I) or (II):

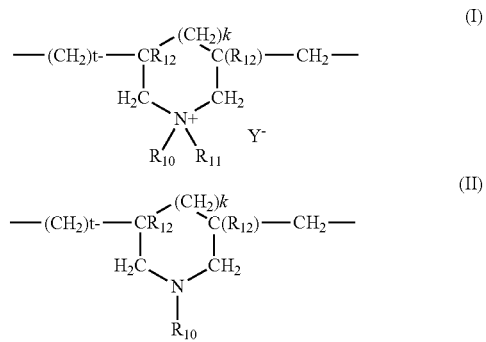

wherein
k and t are equal to 0 or 1, the sum k+t being equal to 1;
R12 denotes a hydrogen atom or a methyl radical;
R10 and R11, independently of each other, denote a C1-C6 alkyl group, a C1-C5 hydroxyalkyl group, a C1-C4 amidoalkyl group; or alternatively R10 and R11 denote, together with the nitrogen atom to which they are attached, a heterocyclic group;
Y—is an anion chosen from bromide, chloride, acetate, borate, citrate, tartrate, bisulfate, bisulfite, sulfate, or phosphate;

(8) quaternary diammonium polymers comprising repeating units of formula:

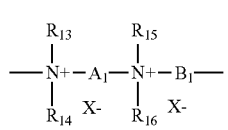

wherein:
  R13, R14, R15 and R16, which may be identical or different:
    i) represent aliphatic, alicyclic or arylaliphatic radicals comprising from 1 to 20 carbon atoms or C1-C12 hydroxyalkyl aliphatic radicals,
    ii) together or separately, form, with the nitrogen atoms to which they are attached, heterocycles optionally comprising a second non-nitrogen heteroatom, or
    iii) represent a linear or branched C1-C6 alkyl radical substituted with a nitrile, ester, acyl, amide or —CO—O—R17—D or —CO—NH—R17—D group, where R17 is an alkylene and D is a quaternary ammonium group;
  A1 and B1 represent linear or branched, saturated or unsaturated, divalent polymethylene groups comprising from 2 to 20 carbon atoms, which optionally comprise, linked to or intercalated in the main chain, one or more aromatic rings or one or more oxygen or sulfur atoms or sulfoxide, sulfone, disulfide, amino, alkylamino, hydroxyl, quaternary ammonium, ureido, amide, or ester groups, and
  X⁻ denotes an anion derived from a mineral or organic acid;
  it being understood that A1, R13 and R15 can form, with the two nitrogen atoms to which they are attached, a piperazine ring;
  in addition, if A1 denotes a linear or branched, saturated or unsaturated alkylene or hydroxyalkylene radical, B1 may also denote a group (CH2)n—CO—D—OC—(CH2)n— with n and p, which may be identical or different, being integers ranging from 2 to 20, and D denoting:
    a) a glycol residue of formula —OZ—O—, in which Z denotes a linear or branched hydrocarbon-based radical, or a group corresponding to one of the following formulae: —(CH2CH2O)x—CH2CH2—and —[CH2CH(CH3)O]y—CH2CH(CH3)-, wherein x and y denote an integer from 1 to 4, representing a defined and unique degree of polymerization or any number from 1 to 4 representing an average degree of polymerization;
    b) a bis-secondary diamine residue, such as a piperazine derivative;
    c) a bis-primary diamine residue of formula —NH—Y—NH—, in which Y denotes a linear or branched hydrocarbon-based radical, or else the divalent radical —CH2—CH2—S—S—CH2—CH2—; or
    d) a ureylene group of formula —NH—CO—NH—;

(9) polyquaternary ammonium polymers comprising units of formula (V):

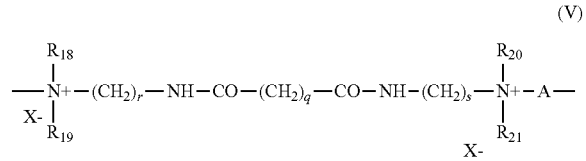

wherein:
  R18, R19, R20 and R21, which may be identical or different, represent a hydrogen atom or a methyl, ethyl, propyl, β-hydroxyethyl, β-hydroxypropyl or —CH2CH2(OCH2CH2)pOH radical, in which p is equal to 0 or to an integer between 1 and 6, with the proviso that R18, R19, R20 and R21 do not simultaneously represent a hydrogen atom,
  r and s, which may be identical or different, are integers between 1 and 6,
  q is equal to 0 or to an integer between 1 and 34,
  X⁻ denotes an anion such as a halide,
  A denotes a divalent dihalide radical or preferably represents —CH2—CH2—O—CH2—CH2—;

(10) Quaternary polymers of vinylpyrrolidone and of vinylimidazole;
(11) polyamines; and/or
(12) polymers comprising in their structure:
  (a) one or more units corresponding to formula (A) below:

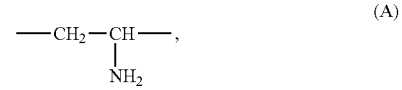

(b) optionally one or more units corresponding to formula (B) below:

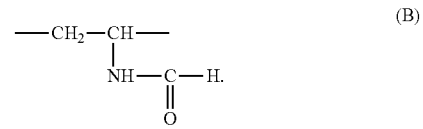

11. The process according to claim 8, comprising at least one silicone, wherein the silicone is chosen from polydialkylsiloxanes.

12. The process according to claim 8, wherein the at least one conditioning agent other than plant waxes and oils is present in the composition in an amount ranging from 0.01% to 20% by weight, relative to the total weight of the composition.

13. The process according to claim 8, wherein the at least one conditioning agent other than plant waxes and oils is present in the composition in an amount ranging from 0.1% to 12% by weight, relative to the total weight of the composition.

14. The process according to claim 1, wherein the at least one oil is chosen from plant oils.

15. The process according to claim 1, wherein the composition is free of reducing agents.

16. The process according claim 1, wherein the heating appliance is a flat iron comprising two arms that are mobile between a closed-together configuration for treating the keratin fibres and an opened-apart configuration.

17. The process according to claim 16, wherein at least one of the arms comprises at least one plate for treating keratin fibres, equipped with a seal.

18. The process according to claim 16, wherein each arm comprises at least one plate for treating keratin fibres, equipped with a seal.

* * * * *